United States Patent [19]
Springer et al.

[11] Patent Number: 6,015,666
[45] Date of Patent: *Jan. 18, 2000

[54] **RAPID DNA TEST FOR DETECTING QUINOLONE-RESISTANT *STAPHYLOCOCCUS AUREUS* PATHOGENS IN CLINICAL MATERIAL**

[75] Inventors: Wolfgang Springer, Wuppertal; Klaus-Dieter Bremm, Recklinghausen; Rainer Endermann, Wuppertal, all of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/477,010

[22] Filed: Jun. 7, 1995

[30] Foreign Application Priority Data

Jun. 23, 1994 [DE] Germany ............... 44 21 901

[51] Int. Cl.[7] ............... C12Q 1/68; C12P 19/34; C07H 21/04
[52] U.S. Cl. ............... 435/6; 435/6; 435/91.2; 536/23.2; 536/23.7; 536/24.32; 536/24.33
[58] Field of Search ............... 435/4, 6, 7.32, 435/7.33, 91.2, 810; 935/6, 8, 77, 78; 536/23.1, 23.7, 24.32, 24.33, 23.2

[56] References Cited

U.S. PATENT DOCUMENTS

| | | | |
|---|---|---|---|
| 4,965,188 | 10/1990 | Mullis et al. ............... | 435/6 |
| 5,462,855 | 10/1995 | Springer et al. ............... | 435/6 |
| 5,496,699 | 3/1996 | Sorenson ............... | 435/6 |

FOREIGN PATENT DOCUMENTS

| | | |
|---|---|---|
| 200362 | 12/1986 | European Pat. Off. . |
| 201184 | 12/1986 | European Pat. Off. . |
| 320308 | 6/1989 | European Pat. Off. . |
| 329822 | 8/1989 | European Pat. Off. . |
| 427074 | 5/1991 | European Pat. Off. . |
| 456047 | 11/1991 | European Pat. Off. . |
| 43 38 119 | 5/1995 | Germany . |
| 2202328 | 9/1988 | United Kingdom . |
| 06270 | 10/1987 | WIPO . |
| 93/18178 | 9/1993 | WIPO . |

OTHER PUBLICATIONS

Ausbel et al, editors of Short Protocols in Molecular Biology John Wiley & Sons, New York (1989), pp. 68–74, 78–78, 113–116.
Tokue et al. Antimic. Agents & Chemo. 38: 428–431 (Mar. 1994).
Williams. Biotechniques 7:762–768, 1989.
Hopewell et al. J. Bacteriol. 172:3481–3484, Jun. 1990.
J.Bacteriol., vol. 172, No. 12, Dec. 1990, p. 6942–6949.
J.Bacteriol., vol. 173, No. 18, Sep. 1991, p. 5854–5860.
M.Nucleic Acids Rs., vol. 17, No. 13, 1989, p. 4937–4946.
Analytical Biochem. 177, 85–89 (1989).
J.Mol. Biol., 113, 237–251 (1977).
Analytical Biochem., 132, 6–13, (1983).
Tetrahedron Letters, vol. 22, No. 20, pp. 1859–1862, 1981.
J.Biol. Chem., vol. 246, No. 4, pp. 909–916, 1971.
J. Goswitz, et al.: "Detection of gyrA Gene ... Sequencing", Antimicrobial Agents and Chemotherapy, Bd. 36, Nr. 5, 1992, pp. 1166–1169.

(List continued on next page.)

*Primary Examiner*—Carla J. Myers
*Assistant Examiner*—Diana Johannsen
*Attorney, Agent, or Firm*—Sprung Kramer Schaefer & Briscoe

[57] ABSTRACT

The invention describes starter oligonucleotide (primers), DNA probes and test methods for rapidly detecting quinolone-resistant *Staphylococcus aureus* pathogens in clinical sample material.

5 Claims, 3 Drawing Sheets

OTHER PUBLICATIONS

C.R. Newton, et al.: "Analysis of any . . . Research", Bd. 17, Nr. 7, Apr. 11, 1989, pp. 2503–2516.

E. Margerrison, et al.: "Nucleotide Sequence . . . Proteins", Journal of Bacteriology, Bd. 174, Nr. 5, 1992, pp. 1596–1603.

S. Sreedharan, et al.: "DNA Gyrase gyrA . . . coli", Journal of Bacteriology, Bd. 172, Nr. 12, 1990, pp. 7260–7262.

C. Fasching, et al.: "gyrA Mutations in . . . Tennessee", Journal of Infectious Diseases, Bd. 164, 1991, pp. 976–979.

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: no

(iv) ANTI-SENSE: no

(vi) ORIGINAL SOURCE:
      (A) ORGANISM: primer
      (C) INDIVIDUAL ISOLATE: synthetic    (xi) SEQUENCE DESCRIPTION: SEQ ID NO:1:

ATCACCCTCA TGGTGACTT                                                  19

(2) INFORMATION FOR SEQ ID NO: 2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: no

(iv) ANTI-SENSE: no

(vi) ORIGINAL SOURCE:
      (A) ORGANISM: primer
      (C) INDIVIDUAL ISOLATE: synthetic    (xi) SEQUENCE DESCRIPTION: SEQ ID NO:2:

ATCACCCTCA TGGTGACG                                                   18

(2) INFORMATION FOR SEQ ID NO: 3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (ii) MOLECULE TYPE: DNA (genomic)

(iii) HYPOTHETICAL: no (iv) ANTI-SENSE:  no (vi) ORIGINAL SOURCE:
             (A) ORGANISM:  primer
             (C) INDIVIDUAL ISOLATE:  synthetic (xi) SEQUENCE DESCRIPTION: SEQ ID NO:3:

ATGGTGACTC ATCTATTTAT A                                                  21

(2) INFORMATION FOR SEQ ID NO: 4:

(i) SEQUENCE CHARACTERISTICS:
             (A) LENGTH:  18 base pairs
             (B) TYPE:  nucleic acid
             (C) STRANDEDNESS:  single
             (D) TOPOLOGY:  linear (ii) MOLECULE TYPE:    DNA (genomic)

(iii) HYPOTHETICAL:  no (iv) ANTI-SENSE:  no (vi) ORIGINAL SOURCE:
             (A) ORGANISM:  primer
             (C) INDIVIDUAL ISOLATE:  synthetic (xi) SEQUENCE DESCRIPTION: SEQ ID NO:4:

GTCCGCCTCC ACGTTCTT                                                      18

(2) INFORMATION FOR SEQ ID NO: 5:

(i) SEQUENCE CHARACTERISTICS:
             (A) LENGTH:  36 base pairs
             (B) TYPE:  nucleic acid
             (C) STRANDEDNESS:  single
             (D) TOPOLOGY:  linear (ii) MOLECULE TYPE:    DNA (genomic)

(iii) HYPOTHETICAL:  no (iv) ANTI-SENSE:  no (vi) ORIGINAL SOURCE:
             (A) ORGANISM:  primer
             (C) INDIVIDUAL ISOLATE:  synthetic (xi) SEQUENCE DESCRIPTION: SEQ ID NO:5:

GTACGTATGG CTCAAGATTT CAGTTATCGT TATCCG                                  36

(2) INFORMATION FOR SEQ ID NO: 6:

(i) SEQUENCE CHARACTERISTICS:
             (A) LENGTH:  534 base pairs
             (B) TYPE:  nucleic acid
             (C) STRANDEDNESS:  single
             (D) TOPOLOGY:  linear (ii) MOLECULE TYPE:    DNA (genomic)

(iii) HYPOTHETICAL:  no (iv) ANTI-SENSE:  no (vi) ORIGINAL SOURCE:
             (A) ORGANISM:  probe
             (C) INDIVIDUAL ISOLATE:  synthetic (xi) SEQUENCE DESCRIPTION: SEQ ID NO:6:

ATCACCCTCA TGGTGACTCA TCTATTTATG AAGCAATGGT                              40

```
ACGTATGGCT CAAGATTTCA GTTATCGTTA TCCGCTTGTT                      80

GATGGCCAAG GTAACTTTGG TTCAATGGAT GGAGATGGCG                     120

CAGCAGCAAT GCGTTATACT GAAGCGCGTA TGACTAAAAT                     160

CACACTTGAA CTGTTACGTG ATATTAATAA AGATACAATA                     200

GATTTTATCG ATAACTATGA TGGTAATGAA AGAGAGCCGT                     240

CAGTCTTACC TGCTCGATTC CCTAACTTGT TAGCCAATGG                     280

TGCATCAGGT ATCGCGGTAG GTATGGCAAC GAATATTCCA                     320

CCACATAACT TAACAGAATT AATCAATGGT GTACTTAGCT                     360

TAAGTAAGAA CCCTGATATT TCAATTGCTG AGTAATGGA                      400

GGATATTGAA GGTCCTGATT TCCCAACTGC TGGACTTATT                     440

TTAGGTAAGA GTGGTATTAG ACGTGCATAT GAAACAGGTC                     480

GTGGTTCAAT TCAAATGCGT TCTCGTGCAG TTATTGAAGA                     520

ACGTGGAGGC GGAC                                                 534

(2) INFORMATION FOR SEQ ID NO: 7:

(i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:    DNA (genomic)

(iii) HYPOTHETICAL:  no (iv) ANTI-SENSE:   no (vi) ORIGINAL SOURCE:
        (A) ORGANISM:  Staphylococcus aureus (xi) SEQUENCE DESCRIPTION: SEQ ID NO:7:

GGTGACTCAT CTATTTATGA AG                                         22

(2) INFORMATION FOR SEQ ID NO: 8:

(i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:    DNA (genomic)

(iii) HYPOTHETICAL:  no (iv) ANTI-SENSE:   no (vi) ORIGINAL SOURCE:
        (A) ORGANISM:  Staphylococcus aureus (xi) SEQUENCE DESCRIPTION: SEQ ID NO:8:

GGTGACTCAT CTATCTATGA AG                                         22

(2) INFORMATION FOR SEQ ID NO: 9:

(i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:    DNA (genomic)
```

```
        (iii) HYPOTHETICAL: no (iv) ANTI-SENSE:   no (vi) ORIGINAL SOURCE:
             (A) ORGANISM:  Staphylococcus aureus (xi) SEQUENCE DESCRIPTION: SEQ ID NO:9:

GGTGACTTAT CTATTTATGA AG                                                22

(2) INFORMATION FOR SEQ ID NO: 10:

(i) SEQUENCE CHARACTERISTICS:
             (A) LENGTH:  22 base pairs
             (B) TYPE:  nucleic acid
             (C) STRANDEDNESS:  single
             (D) TOPOLOGY:  linear (ii) MOLECULE TYPE:    DNA (genomic)

(iii) HYPOTHETICAL: no (iv) ANTI-SENSE:   no (vi) ORIGINAL SOURCE:
             (A) ORGANISM:  Staphylococcus aureus (xi) SEQUENCE DESCRIPTION: SEQ ID NO:10:

GGTGACTTAT CTATCTATGA AG                                                22

(2) INFORMATION FOR SEQ ID NO: 11:

(i) SEQUENCE CHARACTERISTICS:
             (A) LENGTH:  22 base pairs
             (B) TYPE:  nucleic acid
             (C) STRANDEDNESS:  single
             (D) TOPOLOGY:  linear (ii) MOLECULE TYPE:    DNA (genomic)

(iii) HYPOTHETICAL: no (iv) ANTI-SENSE:   no (vi) ORIGINAL SOURCE:
             (A) ORGANISM:  Staphylococcus aureus (xi) SEQUENCE DESCRIPTION: SEQ ID NO:11:

GGTGACTCAT CTATTTATAA AG                                                22

(2) INFORMATION FOR SEQ ID NO: 12:

(i) SEQUENCE CHARACTERISTICS:
             (A) LENGTH:  22 base pairs
             (B) TYPE:  nucleic acid
             (C) STRANDEDNESS:  single
             (D) TOPOLOGY:  linear (ii) MOLECULE TYPE:    DNA (genomic)

(iii) HYPOTHETICAL: no (iv) ANTI-SENSE:   no (vi) ORIGINAL SOURCE:
             (A) ORGANISM:  Staphylococcus aureus (xi) SEQUENCE DESCRIPTION: SEQ ID NO:12:

GGTGATTCAT CTATTTATAA AG                                                22

(2) INFORMATION FOR SEQ ID NO: 13:
```

```
    (i) SEQUENCE CHARACTERISTICS:
        (A) LENGTH:  22 base pairs
        (B) TYPE:  nucleic acid
        (C) STRANDEDNESS:  single
        (D) TOPOLOGY:  linear (ii) MOLECULE TYPE:    DNA (genomic)

(iii) HYPOTHETICAL:  no (iv) ANTI-SENSE:   no (vi) ORIGINAL SOURCE:
        (A) ORGANISM:  Staphylococcus aureus (xi) SEQUENCE DESCRIPTION: SEQ ID NO:13:

GGTGACGCAT CTATTTATGA AG                                                    22
```

RAPID DNA TEST FOR DETECTING QUINOLONE-RESISTANT *STAPHYLOCOCCUS AUREUS* PATHOGENS IN CLINICAL MATERIAL

The invention describes starter oligonucleotides (primers), DNA probes and test methods for rapidly detecting quinolone-resistant *Staphylococcus aureus* pathogens in clinical sample material.

Fluoroquinolones are potent antibacterial agents for treating problematical bacterial infections. Infections due to methicillin-resistant Staphylococci are also treated with fluoroquinolones, for example ciprofloxacin.

However, as was the case with the previous quinolones, for example nalidixic acid, *Staphylococcus aureus* strains are ever more frequently being found which are resistant to fluoroquinolones.

At the same time, many clinics are experiencing problems with methicillin-resistant Staphylococci which have also become resistant to fluoroquinolones. The increase in fluoroquinolone resistance is of particular importance in view of the fact that only a few anti-bacterial agents are effective against infections due to methicillin-resistant and quinolone-resistant Staphylococci.

It is, therefore, particularly important to initiate therapy with the effective antibiotic at as early a stage as possible. The classical diagnosis of quinolone-resistant Staphylococci is time-consuming and labor-intensive, and necessitates the in-vitro cultivation of the strains on plates, followed by physiological identification using test systems such as, for example, "api staph" (BioMérieux) and determination of the antibiotic resistances by means of serial dilution tests (MIC values) or agar diffusion tests (inhibition zone tests). The alternative which is presented here is the development of a gene test based on the QRSA gyrase, which test permits rapid diagnosis directly in the sample material, without any in-vitro cultivation.

Ciprofloxacin is a 4-quinolone antibiotic which inhibits the A2B2 tetramer structure of the enzyme DNA gyrase. DNA gyrase brings about a twisting of the DNA by means of catalysing transient breaks in the DNA double strand.

Mutations in the gyrase A subunit have been demonstrated to be the molecular cause of the quinolone resistance of *Staphylococcus aureus* (Sreedharan, S., M. Oram, B. Jensen, L. R. Peterson, L. M. Fisher, J. Bacteriol. 7260–7262, 1990). Mutations in the nor A gene, which affect a membrane-associated transport mechanism, and thereby prevent the uptake and internal accumulation of the antibiotic (Yoshida, H., M. Bogaki, S., Nakamura, K. Ubukata, N. Konno, J. Bacteriol. 172, 6942–6949, 1990) constitute an additional cause. Over and above this, a mutation has been described in another gene locus which brings about quinolone resistance by means of a mechanism which is still unknown (Trucksis, M., J. S. Wolfson, D. C. Hooper, J. Bacteriol. 173, 5854–5860, 1991).

Since the point mutations which have been described in the serine 84 and serine 85 codons in the staphylococcal gyrase A gene are associated with ciprofloxacin resistance, we have examined the nucleotide region from 2394 to 2658, which encompasses these point mutations, in more detail.

In our investigations of 50 quinolone-resistant *Staphylococcus aureus* isolates having differing MIC values for methicillin and ciprofloxacin, we have detected four types of mutation in gyrase A (see table 1) by means of PCR sequencing with magnetic beads, using the modified method of Hultman T, Stahl, S., Hornes, E., Uhlen, M. Nucleic Acids Res. 17, 4937–4946, 1989. A further type of mutation, based on a point mutation at position 2540, does not result in any amino acid replacement at the protein level and has no influence on the resistance properties of the gyrase. Based on three of the mutations, a point mutation-specific amplification test has been developed for detecting C/T, T/G and G/A mutations.

This test detects all the gyrase mutations in *Staphylococcus aureus* which are relevant for ciproresistance.

TABLE 1

Ciproresistance mutations in the gyrase A sequence of Staphylococcus aureus
Staphylococcus aureus.

Region 2526 to 2547 of the syrase A sequence of Staphylococcus aureus

| | | Cipro-MHK µg/ml |
|---|---|---|
| GGTGACTCATCTATTTATGAAG (SEQ ID NO:7) | STAPH.AUREUS LITERATUR | |
| | STAPH.AUREUS NO.25532 | 0.5 |
| | STAPH.AUREUS NO.25035 | <0.25 |
| | STAPH.AUREUS NO.25085 | 0.25 |
| GGTGACTCATCTATCTATGAAG (SEQ ID NO:8) | STAPH.AUREUS NO.23 | 2.0 |
| | STAPH.AUREUS NO.37 | 2.0 |
| | STAPH.AUREUS NO.3 | 1.0 |
| | STAPH.AUREUS NO.16 | 0.5 |
| | STAPH.AUREUS NO.25470 | 0.5 |
| | STAPH.AUREUS NO.25471 | 0.5 |
| | STAPH.AUREUS NO.133 | <0.25 |
| GGTGACTTATCTATTTATGAAG (SEQ ID NO:9) | STAPH.AUREUS NO.25768 | >128 |
| | STAPH.AUREUS NO.24911 | >128 |
| | STAPH.AUREUS NO.24922 | >128 |
| | STAPH.AUREUS NO.24936 | >128 |
| | STAPH.AUREUS NO.24949 | >128 |
| | STAPH.AUREUS NO.24920 | 128 |
| | STAPH.AUREUS NO.30 | >64 |
| | STAPH.AUREUS NO.25893 | 64 |

TABLE 1-continued

Ciproresistance mutations in the gyrase A sequence of Staphylococcus aureus
Staphylococcus aureus.

Region 2526 to 2547 of the syrase A sequence of Staphylococcus aureus

|  |  | Cipro-MHK |
|---|---|---|
|  | STAPH.AUREUS NO.25894 | 64 |
|  | STAPH.AUREUS NO.25909 | 64 |
|  | STAPH.AUREUS NO.25913 | 64 |
|  | STAPH.AUREUS NO.25921 | 64 |
|  | STAPH.AUREUS NO.25948 | 64 |
|  | STAPH.AUREUS NO.44 | 32 |
|  | STAPH.AUREUS NO.64 | 32 |
|  | STAPH.AUREUS NO.25923 | 32 |
|  | STAPH.AUREUS NO.25912 | 16 |
|  | STAPH.AUREUS NO.25919 | 16 |
|  | STAPH.AUREUS NO.25924 | 16 |
|  | STAPH.AUREUS NO.25926 | 16 |
|  | STAPH.AUREUS NO.25928 | 16 |
|  | STAPH.AUREUS NO.25934 | 16 |
|  | STAPH.AUREUS NO.25906 | 8 |
|  | STAPH.AUREUS NO.25910 | 8 |
| GGTGACTTATCTATCTATGAAG (SEQ ID NO:10) | STAPH.AUREUS NO. 25929 | 64 |
|  | STAPH.AUREUS NO.25703 | 32 |
|  | STAPH.AUREUS NO.24 | 16 |
|  | STAPH.AUREUS NO.25917 | 16 |
|  | STAPH.AUREUS NO.25925 | 16 |
|  | STAPH.AUREUS NO.25930 | 16 |
|  | STAPH.AUREUS NO.25932 | 16 |
|  | STAPH.AUREUS NO.25916 | 8 |
|  | STAPH.AUREUS NO.25927 | 8 |
| GGTGACTCATCTATTTATAAAG (SEQ ID NO:11) | STAPH.AUREUS NO. 25915 | 64 |
|  | STAPH.AUREUS NO.25918 | 16 |
| GGTGATTCATCTATTTATAAAG (SEQ ID NO:12) | STAPH.AUREUS NO. 25914 | 32 |
| GGTGACGCACTATTTATGAAG (SEQ ID NO:13) | STAPH.AUREUS NO.25908 | 16 |

| TCA | > TTA | ATT | > ATC | GAA | > AAA |
|---|---|---|---|---|---|
| SERIN | > LEUCIN | ISOLEUCIN | > ISOLEUCIN | GLUTAMIN | > LYSIN |
| TCA | > GCA | GAC | > GAT |  |  |
| SERIN | > ALANIN | ASPARAGIN | > ASPARARGIN |  |  |

150 different quinolone-resistant Staphylococci (QRSA) (including the strains in table 1) having MIC values of between four and 128 µg/ml (see also table 2) were analysed using this gene test. 92.1% of the strains have the mutation C/T in position 2533. Four strains (2.6%) have the mutation T/G in position 2532 and three strains (2%) have the mutation G/A in position 2544. Five strains (3.3%) have other mutations which are not situated in the gyrase, as was established by subsequently subjecting these strains to PCR sequencing.

A detection sensitivity of 96.7% is thus obtained for this test based on detecting the three mutations.

TABLE 2

Gen testing of QRSA

|  | Methicilin MIC | Cipro-MIC | QRSA gene test |
|---|---|---|---|
| *Staphylococcus aureus* |  |  |  |
| 811 | >32 | 32 | C/T |
| 794 | >32 | 16 | C/T |

TABLE 2-continued

Gen testing of QRSA

|  | Methicilin MIC | Cipro-MIC | QRSA gene test |
|---|---|---|---|
| 822 | >32 | 16 | — |
| 818 | >32 | >64 | C/T |
| 807 | 32 | 64 | C/T |
| 830 | 16 | >64 | C/T |
| 801 | >32 | 32 | C/T |
| 804 | >32 | >64 | C/T |
| 800 | >32 | 16 | G/A |
| 793 | 16 | >64 | C/T |
| 788 | >32 | 64 | C/T |
| 792 | >32 | >64 | C/T |
| 789 | >32 | 64 | C/T |
| 798 | 32 | >64 | C/T |
| 843 | >32 | >64 | C/T |
| 838 | 4 | 16 | T/G |
| 784 | >32 | 32 | — |
| 813 | 8 | >64 | C/T |
| 791 | >32 | 32 | C/T |
| 844 | 16 | >64 | C/T |
| 821 | 32 | 16 | — |

TABLE 2-continued

Gen testing of QRSA

| | Methicilin MIC | Cipro-MIC | QRSA gene test |
|---|---|---|---|
| 845 | >32 | 64 | C/T |
| 816 | >32 | 64 | C/T |
| 815 | >32 | 64 | C/T |
| 833 | >32 | 64 | — |
| 814 | >32 | 64 | C/T |
| 839 | 32 | 64 | C/T |
| 834 | >32 | 64 | C/T |
| 829 | >32 | 64 | C/T |
| 828 | >32 | >64 | C/T |
| 827 | >32 | 32 | C/T |
| 826 | >32 | 64 | C/T |
| 825 | >32 | 64 | C/T |
| 837 | >64 | >32 | C/T |
| 836 | >32 | >64 | C/T |
| 790 | >32 | 64 | — |
| 787 | >32 | >64 | C/T |
| 846 | 32 | 64 | C/T |
| 842 | >32 | 64 | C/T |
| 841 | >32 | 64 | C/T |
| 785 | >32 | >64 | C/T |
| 835 | >32 | >64 | C/T |
| 808 | >32 | >64 | C/T |
| 803 | >32 | >64 | C/T |
| 797 | >32 | >64 | C/T |
| 795 | 32 | 64 | C/T |
| 802 | >32 | >64 | C/T |
| 817 | >32 | 64 | C/T |
| 812 | >32 | >64 | C/T |
| 810 | >32 | >64 | C/T |
| 824 | >32 | >64 | |
| 823 | 32 | 64 | C/T |
| 819 | >32 | >64 | C/T |
| Quinolone-sensitive strains | | | |
| 25532 | 16 | 0.25 | — |
| 25035 | 4 | 0.25 | — |
| 25085 | 64 | 0.25 | — |
| 133 | 0,25 | 0.25 | — |
| 25470 | 32 | 0.5 | — |
| 25471 | 0,5 | 0.5 | — |
| 16 | 32 | 0.5 | — |

The present invention describes specific primers and oligonucleotide probes and polynucleotide probes, and their use for rapidly detecting quinolone-resistant Staphylococci directly in clinical sample material.

1. The primers were prepared by chemical synthesis from the gene sequence of the gyrase A gene.

The preferred primers were selected from the region
a) which is specific for the mutation type C/T (primer 1 SEQ ID NO: 1)
b) which is specific for the mutation type T/G (primer 2 SEQ ID NO: 2)
c) which is specific for the mutation type G/A (primer 3 SEQ ID NO. 3)
d) which is specific for quinolone-resistant and sensitive gyrase as a complementary strand primer (Primer 4 SEQ ID NO: 4)

2. The oligonucleotide probe was prepared by chemical synthesis (SEQ ID NO: 5) from the region 2553–2588. This region is amplified by all the primers and is specific for *S. aureus*. The alternative polynucleotide probe (SEQ ID NO: 6) was prepared by subjecting the nucleotide region 2515 to 3048 to PCR amplification.

3. The genomic DNA of quinolone-resistant strains was isolated using nucleic acid methods which were adapted for Staphylococci.

4. Parts of the gyrase A gene were amplified using the specific primers 1–3 from the coding region, which primers carry the base of the resistance mutation (T instead of C, G instead of G) at the 3' end, and a specific primer 4 from the non-coding strand of the gyrase A gene, which primer is employed as the complementary strand primer for all the amplifications.

5. Amplification was carried out using known amplification techniques, preferably the PCR DNA amplification method (EP 200362).

6. The specific amplification product was detected by
a) direct electrophoresis of the amplification product in an agarose gel and staining with intercalating agents such as ethidium bromide,
b) determination of the fluorescence of the amplification product, which is labelled during the amplification with fluororescence nucleotides or fluorescence-labelled primers. The amplification product is separated off using biotin which has also been incorporated (primer to nucleotide),
c) hybridization of the amplification product, which is labelled during the amplification, to the abovementioned biotinylated oligonucleotide probe. The hybridization complex is separated off using streptavidin-coated magnetic particles,
d) the hybridization complex which has been formed is assessed, as a measure of the quantity or the presence of quinolone-resistant Staphylococci, by means of a chemiluminescence test using anti-digoxigenin antibodies which are coupled to alkaline phosphatase.

If an external, co-amplified staphylococcal DNA standard is used, the assessment may be employed semiquantitatively in order to ascertain the quantity of quinolone-resistant Staphylococci in the clinical sample material.

Gene-probe diagnosis, particularly in conjunction with amplification techniques, is a rapid, specific and highly sensitive method which permits early identification of the pathogens at the DNA/RNA level. The technique can be performed directly on the material under investigation without any in-vitro cultivation. It is based on the DNA/RNA hybridization technique, i.e. on the specific in-vitro binding of complementary single-strand nucleic acid, with the formation of Watson-Crick base pairs. The DNA/DNA or DNA/RNA double strands which are formed are termed hybrids. Complementary, sequence-specific gene probes are used to detect the specific DNA or RNA of a pathogen by the hybridization reaction. These gene probes are either short, chemically synthesized oligonucleotide probes of 10–50 nucleotides in length, or DNA/RNA fragments of 0.5–10 kb which have been prepared by recombinant gene techniques.

The gene probes can be provided, photochemically (N. Dattagupta, P. M. M. Rae, E. D. Huguenel, E. Carlson, A. Lyga, J. S. Shapiro, J. P. Albarella, Analytical Biochem. 177, 85, 1989) or enzymically by nick translation (Rigby, P. W. J. et al, J. Mol. Biol. 113, 237, 1977) or random primed techniques (Feinberg and Vogelsteil, Anal. Biochem. 132, 6, 1983), with a radioactive or non-radioactive label. Labelling with $^{32}$P-NTPs, or non-radioactive labelling with digoxigenin-dUTP, biotin-dUTP or fluorescein-dUTP, or direct labelling with enzymes such as alkaline phosphatase or horseradish peroxidase, are suitable for this purpose.

In order to achieve specific hybridization between the nucleic acid of the pathogen to be detected and the pathogen-specific gene probe, the nucleic acids are first separated into single strands by means of denaturation (heat or alkali treatment), and then quite specifically hybridized to each other under stringent conditions, which are achieved by means of the temperature, the ionic strength of the buffers, and the organic solvents. Under appropriate hybridization conditions, the gene probe only binds to complementary sequences of the DNA or RNA to be detected. This hybridization reaction can be carried out in a variety of test configurations, for example as a solid-phase hybridization of target DNA or gene probe which is coupled to a support such as nitrocellulose, or as a liquid hybridization. Evaluation (readout) is effected by way of labelling the gene probe with a reporter molecule, as mentioned above, or, as in the reversed phase hybridization system presented here, by way of the target DNA, which is labelled with digoxigenin-dUTP during the amplification, and the gene probe, which is labelled with biotin to permit binding to magnetic particles. The hybridization complex composed of target DNA and labelled gene probe is quantitatively determined, once non-bound gene probe has been removed, by way of the reported molecule which is used. This readout can be effected directly in the case of fluorescence labelling or radioactive labelling, or indirectly by means of enzyme tests and immunological methods using antibody conjugates which contain enzymes such as alkaline phosphatase and then make possible a colour reaction or a chemiluminescence reaction.

The test sensitivity achieved using this gene-probe diagnosis is in the range of from $10^5$ to $10^6$ microorganisms, based on the detection of single genes. The test sensitivity can be increased by combining the test with DNA or RNA amplification techniques, such as the PCR (EP 200362), LCR (EP 320308), NASBA (EP 329822), Qβ (PCT 87/06270) or HAS (EP 427074) techniques. Using these techniques, the DNA to be detected can be multiplied up to $10^9$ times. In this way, by combining amplification and hybridization, it becomes possible to detect individual DNA molecules.

Since organism numbers of $10^1$–$10^3$-organisms/ml are found in the blood in infections, this technology provides the possibility of recognising quinolone-resistant infections at an early stage.

In addition to this, the present invention describes the use of these primers, oligonucleotide probes and polynucleotide probes, and test methods for detecting ciproresistant Staphylococci in clinical sample material. An additional advantage of this method is that it provides the possibility of semiquantitatively determining the quantity of quinolone-resistant infectious organisms in the sample material.

Selection and Synthesis of Primers

The nucleotide sequences of the gyrase A gene or the quinolone-resistant *Staphylococcus aureus* isolates listed in table 1 were employed for selecting suitable specific primers. Based on these mutation sequences and on the wild-type nucleotide sequence (E. E. C. Margerrison, R. Hopewell, L. M. Fisher, J. Bacteriol. 1596–1603, 1992), primers were selected which carry the base of the point mutation at the 3' end. The primer SEQ ID NO: 1 was synthesized for the mutation type C/T. The primer 2 SEQ ID NO: 2 was synthesized for the mutation type T/G. The primer SEQ ID NO: 3 was synthesized for the mutation type G/A. The primer 4 SEQ ID NO: 4, which is common to all the primer sets (primers 1+4, 2+4 and 3+4), was synthesized as the complementary strand primer for amplifying the sequence carrying the mutation.

The selected primers were chemically synthesized using the phosphoramidite method of S. L. Beaucage and M. Caruthers, Tetrahedron Letters, 22, 1859, 1981.

Amplification of Genomic QRSA DNA

In order to amplify parts of the gyrase A gene, the abovementioned primers were used, in each case as primer set 1 (primer 1+4), primer set 2 (primer 2+4) and primer set 3 (primers 3+4), to specifically amplify the three mutation types of the QRSA gyrases. Where used with the genomic DNA of quinolone-sensitive gyrase genes, they do not yield any amplification product which is visible in the agarose gel. When the three primer sets are used, the genomic DNA which in each case contains the gyrase gene having the corresponding mutation gives a strong amplification band, thereby demonstrating not only quinolone resistance but also, at the same time, the point mutation which is present in the gyrase.

During the PCR amplification, digoxigenin-dUTP can, for example, also be incorporated into the amplification product in addition to the four dNTPs (deoxyadenosine triphosphate, deoxyguanosine triphosphate, deoxycytidine triphosphate and thymidine triphosphate). As a result, the amplification product can be read using an anti-digoxigenin antibody, which is coupled to alkaline phosphatase, for example, by way of chemiluminiscence test using AMPPD as substrate or by means of a stain test using bromochloroindolyl phosphate and nitroblue tetrazolium or para-nitrophenylphosphate.

Alternatively, the possibility exists of incorporating fluorescence-labelled nucleoside triphosphates, such as fluorescein-dUTP or coumarin-dUTPs, into the amplification product, thereby identifying the amplification product with much greater sensitivity than when ethidium bromide staining is used. Then, when biotinylated primers are used, the possibility exists of separating off the fluorescence-labelled, biotinylated amplification product using streptavidin-coated magnetic particles, and determining it quantitatively in a fluorescence photometer.

Selection and Synthesis of the Oligonucleotide Probe

The oligonucleotide probe which was specific for the amplification products of the primer sets was selected from the region 2553–2588, which is common to all the three mutation-specific amplification products. A 36 mer was synthesized which has the sequence SEQ ID NO: 5 and which is specific for the three amplification products.

It was chemically synthesized using the phosphoramidite method of S. L. Beaucage and M. Caruthers, Tetrahedron Letters, 22, 1859, 1981.

The oligonucleotide probe can specifically hybridize to the mutation-specific amplification products. The method in which parts of the gyrase A gene are initially amplified using the mutation-specific primers, and the amplification product is then specifically hybridized to the oligonucleotide probe has the following advantages as compared with straightforward amplification diagnosis:

When the amplification product is directly read in the gel, the test sensitivity is approximately 1000 organisms/ml of sample material. By contrast, in combination with hybridization to the oligonucleotide probe and a chemiluminscence readout, a detection of 10 organisms/ml of sample material is achieved.

Selection and Synthesis of an Alternative Polynucleotide Probe

As an alternative to the oligonucleotide probe, a polynucleotide probe of 534 bases was selected from the nucleotide sequence 2515–3048, which is common to all the mutation-specific amplification products. The polynucleotide probe was synthesized by PCR amplification using primer 1 (SEQ ID NO: 1) and primer 4 (SEQ ID NO: 4). During the amplification, biotin-dUTP for the chemiluminescence test was simultaneously incorporated into the amplified gene probe.

Detection of QRSA

Directly after amplifying parts of the gyrase A gene by means of the three primer sets described in the invention, the QRSA can be determined using any desired analysis methods.

One possible readout method consists of staining the amplification product, which has been separated by agarose gel electrophoresis, with intercalating agents such as ethidium bromide.

Another possibility is to incorporate fluorescence-labelled nucleoside triphosphates into the amplification product. This result in a marked improvement in the test sensitivity.

A further possibility is to use fluorescence-labelled primers for the amplification, or to combine biotinylated primers with fluorescence nucleotides, so that a terminally biotinylated, fluorescence-labelled amplification product result which can be bound to streptavidin-coupled magnetic particles, and separated, and the fluorescence can be terminated semiquantitatively.

The most sensitive method, which at the same time permits a semiquantitative readout, is the described method of hybridizing the amplification products of the three mutation-specific primer sets to the described oligonucleotide probe. This method also makes it possible to quantify the QRSA in clinical sample material. When, for example, digoxigenin-dUTP is incorporated during the amplification, and a biotinylated oligonucleotide probe is used, the hybridization complex can be separated on streptavidin-coated magnetic particles and, when antidigoxigenin antibodies which are coupled to alkaline phosphatase are used, the complex can be read semiquantitatively by means of chemiluminescence using AMPD as substrate. If, at the same time, samples containing defined numbers of cells are coamplified as cell standards and read in the chemiluminescence test, the organism number can then be determined semiquantitatively from the chemiluminescence signals emitted by the clinical sample material.

EXAMPLE 1
Synthesis of Starter Oligonucleotides (Primers)

The selected starter oligonucleotides (primers) were chemically synthesized using the phosphoramidite method of S. L. Beaucage and M. Caruthers, Tetrahedron Letters, 22, 1859, 1981. The following nucleotide sequences were synthesized:

PCR primer 1, specific for mutation C/T: SEQ ID NO: 1

PCR primer 2, specific for mutation T/G: SEQ ID NO: 2

PCR primer 3, specific for mutation G/A: SEQ ID NO: 3

PCR primer 4, complementary strand primer for all the mutations: SEQ ID NO: 4

EXAMPLE 2
Synthesis and Selection of the Oligonucleotide Probe for QRSA

The oligonucleotide probe was selected from the nucleotide region 2553–2588, which is contained in all the mutation-specific amplification products and is specific for the gyrase A of Staphylococcus aureus.

The selected oligonucleotide probe was chemically synthesized using the phosphoramidite method of S. L. Beaucage and M. Caruthers, Tetrahedron Letters, 22, 1859, 1981. The following nucleotide sequence was synthesized: GTACGTATGGCTAAGATTTCAGTTATCGTTATCCG, 36 mer oligonucleotide from nucleotide region 2553–2588, SEQ ID NO: 5.

The oligonucleotide probe was labelled at its 3' end using the method of Bollum, The Enzymes, Boyer ed, Vol 10, p 145 Academic Press, New York. The endgroup labelling was carried out non-radioactively using biotin-dUTP. (Chang, L. M. S., Bollum T. J., J. Biol. Chem. 246,909,1971).

Approximately 50% 3' end-labelling is achieved after 60 minutes in a 50 µl mixture which contains 10 µl of reaction buffer (potassium cacodylate, 1 mol/l; Tris/HCl, 125 mmol/l; bovine serum albumin, 1.25 mg/ml; pH6.6; 25° C.), 1–2 µg of oligonucleotide, 25 units of terminal transferase, $CoCl_2$, 2.5 mmol/l and 1 µl of biotin-dUTP (1 mmol/l) and is incubated at 37° C.

EXAMPLE 3
Synthesis and Selection of a Polynucleotide Probe for QRSA

The polynucleotide probe was selected from the polynucleotide region 2515 to 3048, which is contained in all the mutation-specific amplification products and is specific for the gyrase A of S. aureus.

It was synthesized by PCR amplification using primer 1 (SEQ ID NO: 1) and primer 4 (SEQ ID NO: 4) in accordance with example 4. For the chemiluminescence test in accordance with example 6, biotin-dUTP was incorporated into the amplified gene probe during the amplification.

EXAMPLE 4
The QRSA-specific DNA Amplification by PCR

The target DNA was amplified by the polymerase chain reaction (EP 200362; 201184).

The following were employed in the PCR reaction: 10 pg of genomic DNA for quinolone-resistance Staphylococci, 0.17 µmol of primers 1–4, SEQ ID NO: 1–4, 2.5 units of Cetus/Perkin-Elmer Taq polymerase and 200 µmol/l of each dNTP of a total of 100 µl of PCR buffer (50 mM KCl, 10 mM Tris/HCl, pH 8.3, 2 mM $MgCl_2$ and 0.01% gelatin). The amplification was carried out in a PCR processor from Cetus/Perkin-Elmer. In all, three PCR samples were prepared specifically for the three gyrase mutations and contained primer set 1 (primers 1+4), primer set 2 (primers 2+4) and primer set 3 (primers 3+4), respectively.

For the chemiluminescence test in accordance with example 6, 0.15 µmol of digoxigenin-dUTP was also included in the PCR in order to label the PCR product.

An initial melting of the DNA for 2 minutes 30 seconds at 95° C. was first carried out on the samples, and this was then followed, per cycle, by 1 minute at 95° C. for the DNA denaturation, 1 minute at 58° C. for the primer annealing and 1 minute at 72° C. for the primer extension. After 25 cycles, the samples were cooled directly at 4° C.

EXAMPLE 5
Direct Evaluation of the Amplification Product

In order directly to evaluate the DNA amplification product, either intercalating agents such as ethidium bromide were used after the amplification, or fluorescent nucleoside triphosphates, such as fluorescein-dUTP or hydroxycoumarin-dUTP, were incorporated during the amplification. Biotin-dUTP or digoxigenin-dUTP can also be employed, and a strain readout performed using alkaline phosphatase coupled to antibody. Primers which have been appropriately labelled with fluorescence markers can also be used if the sensitivity is low.

The amplification product was loaded onto an 0.8% agarose gel and electrophoresed at 100 mA for 30 minutes. The fluorescence signals of quinolone-sensitive and quinolone-resistant Staphylococci were directly evaluated under a UV transilluminator.

EXAMPLE 6
Chemiluminescence Gene-probe Test of DNA Amplification Products

A significant increase in sensitivity as compared with that of conventional gene-probe readout methods is achieved by combining suitable target amplification methods such as the polymerase chain reaction (PCR) (EP 200362) and LCR (EP 320308) with the gene-probe technique.

The liquid hybridization tests were carried out as reversed phase tests using 100 ng of 3'-biotinylated gene probes and amplified DNA in accordance with example 4 in a volume of 50 μl.

After heating at 100° C. for 10 minutes, and then cooling down to 0° C., 50 μl of 2×hybridization mix (50 ml of 20×ssC, 1 g of blocking reagent (Boehringer), 2 ml of 10% lauroyl sarcosine and 200 μl of 20% SDS made up to 100 ml with double distilled $H_2O$) were added and hybridization (oligonucleotide probe) was carried out at 37° C. for 5–10 minutes. The magnetic beads were pretreated with 1× hybridization mix and, after they had been separated using a magnet, the liquid was pipetted off; the hybridization sample and 100 μl of 1× hybridization mix were added, and the mixture was incubated at room temperature for 5–10 minutes while being moved gently. The coupled hybridization complex was separated together with the beads and the residual liquid was pipetted off; the beads were then washed 1× with buffer B (0.1 SSC; 0.1% SDS).

The blocking reaction and the antibody reaction for detecting the hybridization by means of chemiluminescence were then carried out. The beads charged with DNA were treated 1× with 500 μl of buffer 2 (0.1 M maleic acid: 0.15 M NaCl, pH 7.5; 1% blocking reagent (Boehringer)). After 5 minutes of incubation at room temperature, the beads were separated off and the liquid was pipetted off; 250 μl of antibody conjugate solution (AC 1:2500 in buffer 2) were added and the mixture was incubated at room temperature for 10 minutes; the beads were then separated off and the liquid was pipetted off, the beads were then treated 2× for 30 seconds and 1× for 2 minutes with 500 μl of washing buffer, while being moved gently. The beads were then incubated in a water bath at 37° C. for 10 minutes with 100 μl of detection solution containing AMPPD of 1:100 in buffer 3, and the chemiluminescence was then measured in a luminescence photometer at 477 nm (Lumacounter from Lumac).

DNA quantities corresponding to from $10^6$ to $10^1$ Staphylococcus organisms can be detected using this test. The same detection limit of 10 organisms per ml of blood was also achieved after adding non-specific blood DNA. Blood DNA on its own only gives rise to low background signals in the hybridization test.

EXAMPLE 7
Isolation of Staphylococcal Nucleic Acid

The sample material infected with Staphylococci, for example infected blood, was centrifuged for 5–10 minutes at 8000 rpm, and the supernatant was pipetted off and discarded. 50 μl of TE containing 15% sucrose were added to the sediment (approximately 180–200 μl), followed by 20 μl of lysozyme+lysostaphin (10+5 mg/ml in double distilled $H_2O$); the mixture was then incubated at 37° C. for 15 minutes. Subsequent working up was carried out using a Quiamp DNAkit from Quiagen. After adding 25 μl of proteinase K and 235 μl of AL buffer, the ingedients were mixed and treated at 70° C. for 10 minutes. The mixture was then cooled in ice, and 240 μl of 100% ethanol were added; after the ingredients had been mixed briefly, they were loaded onto the Quiagen column. The column was then centrifuged for 1 minute at 8000 rpm and the eluate discarded. 700 μl of AW washing buffer were then loaded onto the column, which was centrifuged once again for 1 minute at 8000 rpm. The column was then washed once again with the same quantity of AW buffer, and centrifuged for 1 minute at 8000 rpm and for 10 seconds at 14000 rpm, and the eluate discarded. 200 μl of double distilled $H_2O$ were then loaded onto the column which was centrifuged for 1 minute at 8000 rpm. The eluate contains the purified nucleic acid solution which can be employed for the amplification.

EXAMPLE 8
Detection of QRSA in Clinical Sample Material

The QRSA DNA was isolated from the clinical sample material in accordance with the method described in example 7. The staphylococcal DNA lysate was then amplified by suitable amplification methods using QRSA-specific oligonucleotide primers, as described in example 4. The amplified nucleic acid was hybridized to the oligonucleotide probe SEQ ID NO: 5, and the specific hybridization complex, which forms under stringent conditions and which is composed of amplified staphylococcal nucleic acid and gene-probe DNA, was separated off using Dynal magnetic particles, and determined quantitatively by means of chemiluminescence readout, as in example 6.

Gyrase A gene-specific hybridization signals were still detected in the blood lysates infected with QRSA at a concentration of $10^1$ organisms.

EXAMPLE 9
Quantitative Detection of QRSA

QRSA were isolated from clinical sample material, for example blood, as in example 7, and a chemiluminescence test was carried out following amplification as described in examples 4 and 6. In addition to the clinical samples, samples containing QRSA DNA corresponding to cell numbers of from $10^6$ to $10^0$ cells, in the presence of 500 ng of blood DNA, were amplified in parallel and analysed in the chemiluminescence test. The chemiluminescence signals of the cell standards of from $10^6$ to 10 QRSA in blood were compared with the test samples, containing $10^3$ and $10^2$ organisms, which were analysed in parallel and which had been detected in the test using three sets of primers. The chemiluminescence signals from the cell number DNA standard ($10^3$ and $10^2$) agree very well with the chemiluminescence signals of the test samples containing $10^3$ and $10^2$ organisms, and demonstrate that the chemiluminescence test can be employed for measuring QRSA, for example in blood, semiquantitatively.

DESCRIPTION OF THE FIGURES

FIG. 1

Direct evaluation of the amplification test. The DNA from three quinolone- resistant S. aureus pathogens and from a quinolone-sensitive wild strain, corresponding to $10^3$ cells, was amplified using the point mutation-specific primer sets primer set 1 (primers SEQ ID NO: 1 and SEQ ID NO: 4), primer set (primers SEQ ID NO: 2 and SEQ ID NO: 4) and primer set 3 (SEQ ID NO: 3 and SEQ ID NO: 4), and then analysed by agarose gel electrophoresis. A band is only visible in the agarose gel strained with ethidium bromide when the resistant strain contains the corresponding point mutation in its gyrase A gene. The quinolone- sensitive S. aureus wild type (WT25035) does not give any amplification band with the three primer sets since there is no point mutation in the wild-type gyrase. The S. aureus strain 25768 has a C/T mutation, the strain 25908 a T/G mutation and the strain 25908 a T/G mutation and the strain 25918 a G/A mutation.

FIGS. 2A and 2B

The DNA from three quinolone-resistant S. aureus pathogens, 25768 (1), 25908 (2) and 25918 (3), corresponding to approximately 1000 cells (FIG. 2A) or approximately 100 cells (FIG. 2B), and from a quinolone-sensitive *S. aureus* wild type (25035 (4)), was amplified using the point mutation-specific primer sets 1–3 (SEQ ID NO: 1–4), with digoxigenin-dUTP being simultaneously incorporated into the amplification product. The amplification products were hybridized to a biotinylated oligonucleotide probe (SEQ ID NO: 5), and the hybridization complex was separated off using streptavidin-coated magnetic particles. The formation of the amplification product was measured by means of the chemiluminescence signal in accordance with Example 6. A chemiluminescence signal is only obtained when the resistant strain contains the corresponding point mutation in the gyrase A gene and, for that reason, was amplified by the corresponding primer pair 1, 2 or 3. The quinolone-sensitive *S. aureus* strain 25035 does not give any chemiluminescence signal with the three primer sets since there is no point mutation in the wild-type gyrase. The *S. aureus* strain 25768 is resistant due to a C/T mutation, the strain 25908 is resistant due to a T/G mutation and the strain 25918 is resistant due to a G/A mutation, as is evident from the amplification obtained using the appropriate primer sets.

Figure 1:
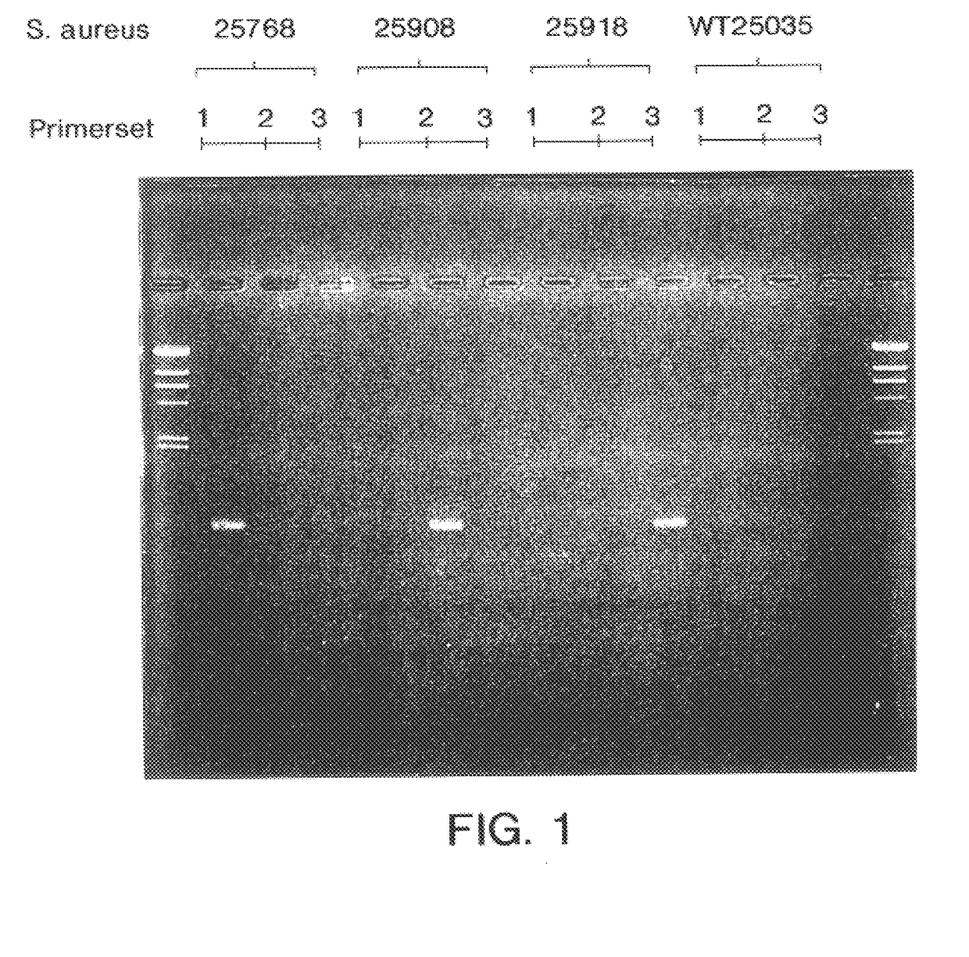
Figure 2A:
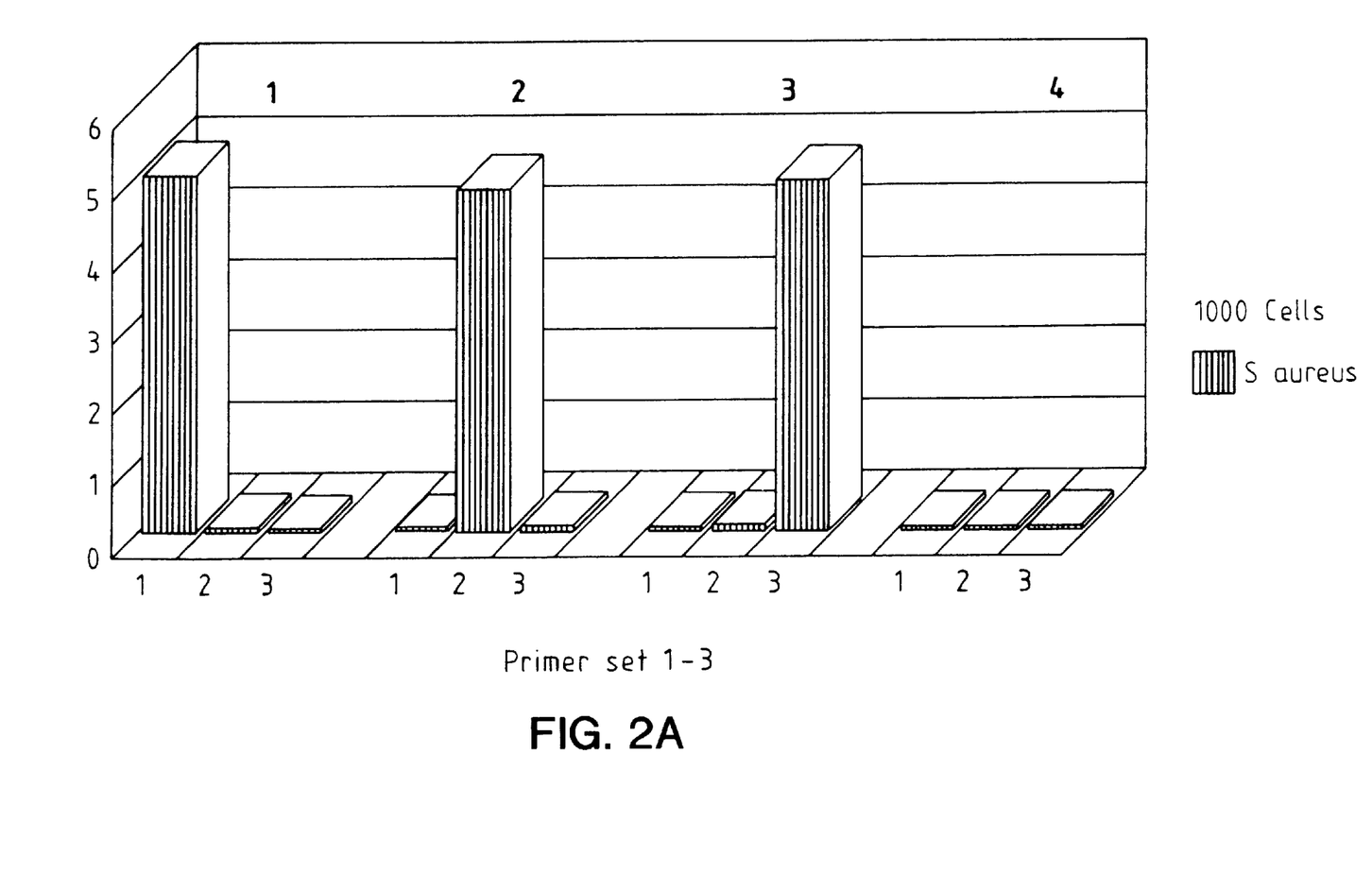
Figure 2B:
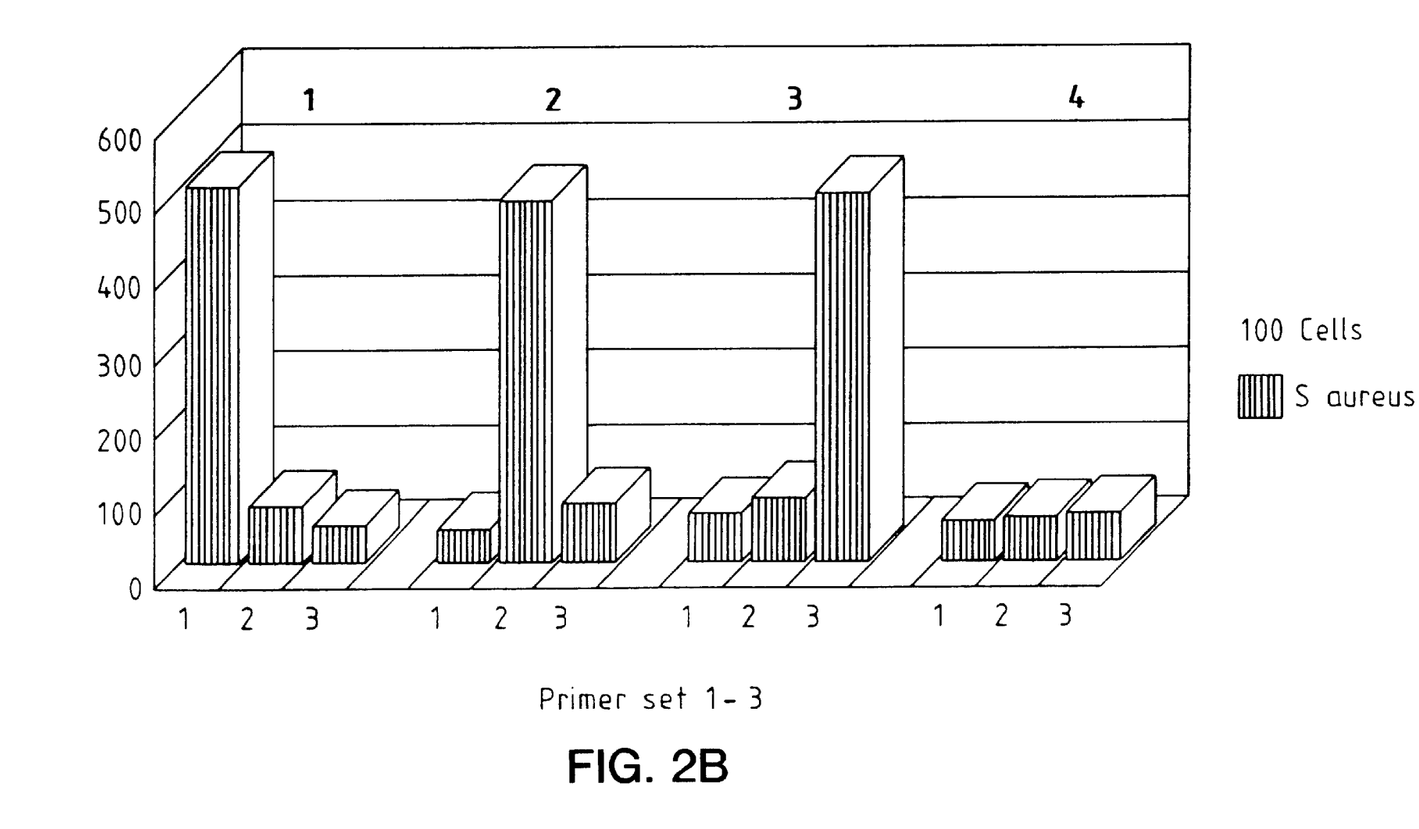

We claim:

1. A method for detecting quinolone-resistant *Staphylococcus aureus* organisms in a sample material, said method comprising the following steps:
   a) amplifying quinolone-resistant *Staphylococcus aureus* DNA or RNA in said sample material using amplification primers consisting of optionally labeled SEQ ID NOS.: 1–4 to yield amplified quinolone-resistant *Staphylococcus aureus* DNA or RNA by a method consisting essentially of:
      i) dividing the sample material into at least three portions;
      ii) incorporating a first primer set consisting of optionally labeled SEQ ID NO.: 1 and optionally labeled SEQ ID NO.: 4 into a first portion of said sample material, and thereafter conducting an amplification reaction on said first portion of said sample material;
      iii) incorporating a second primer set consisting of optionally labeled SEQ ID NO.: 2 and optionally labeled SEQ ID NO.: 4 into a second portion of said sample material, and thereafter conducting an amplification reaction on said second portion of said sample material; and
      iv) incorporating a third primer set consisting of optionally labeled SEQ ID NO.: 3 and optionally labeled SEQ ID NO.: 4 into a third portion of said sample material, and thereafter conducting an amplification reaction on said third portion of said sample material; and
   b) determining the presence of amplified quinolone-resistant *Staphylococcus aureus* DNA or RNA resulting from step a) to give an indication of the presence of quinolone-resistant *Staphylococcus aureus* organisms in said sample material by a method comprising:
      i) detecting the amplified quinolone-resistant *Staphylococcus aureus* DNA or RNA directly, wherein the presence of the amplified quinolone-resistant *Staphylococcus aureus* DNA or RNA indicates that the sample material contains quinolone-resistant *Staphylococcus aureus* organisms; or
      ii) hybridizing the amplified quinolone-resistant *Staphylococcus aureus* DNA or RNA with an oligonucleotide probe consisting of labeled SEQ ID NO.: 5, or with a polynucleotide probe consisting of labeled SEQ ID NO.: 6, under conditions suitable to form a hybridization product of said oligonucleotide probe or said polynucleotide probe and said amplified quinolone-resistant *Staphylococcus aureus* DNA or RNA, and thereafter detecting the presence of the hybridization product by detecting the label, wherein the detection of the hybridization product indicates that the sample material contains quinolone-resistant *Staphylococcus aureus* organisms.

2. The method according to claim 1, wherein the amplification is of parts of the gyrase A gene.

3. The method according to claim 1, wherein the oligonucleotide probe is utilized.

4. The method according to claim 1, wherein the polynucleotide probe is utilized.

5. A test kit consisting essentially of:
   a) a set of amplification primers consisting of optionally labeled SEQ ID NOS.: 1–4; and
   b) optionally at least one hybridization probe selected from the group consisting of:
      i) labeled SEQ ID NO.: 5; and
      ii) labeled SEQ ID NO.: 6.

* * * * *